United States Patent
Mabotuwana et al.

(10) Patent No.: US 11,630,874 B2
(45) Date of Patent: Apr. 18, 2023

(54) METHOD AND SYSTEM FOR CONTEXT-SENSITIVE ASSESSMENT OF CLINICAL FINDINGS

(71) Applicant: KONINKLIJKE PHILIPS N.V., Eindhoven (NL)

(72) Inventors: Thusitha Dananjaya De Silva Mabotuwana, Bothell, WA (US); Yuechen Qian, Lexington, MA (US); Ranjith Naveen Tellis, Cambridge, MA (US); Gabriel Ryan Mankovich, Boston, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 567 days.

(21) Appl. No.: 15/550,812

(22) PCT Filed: Feb. 19, 2016

(86) PCT No.: PCT/IB2016/050893
§ 371 (c)(1),
(2) Date: Aug. 14, 2017

(87) PCT Pub. No.: WO2016/135598
PCT Pub. Date: Sep. 1, 2016

(65) Prior Publication Data
US 2018/0032676 A1 Feb. 1, 2018

Related U.S. Application Data

(60) Provisional application No. 62/120,391, filed on Feb. 25, 2015.

(51) Int. Cl.
*G16H 30/40* (2018.01)
*G06F 16/9535* (2019.01)
(Continued)

(52) U.S. Cl.
CPC ...... *G06F 16/9535* (2019.01); *G06F 16/9038* (2019.01); *G06F 16/90335* (2019.01);
(Continued)

(58) Field of Classification Search
CPC .................. G06Q 50/22–24; G06F 16/9535
See application file for complete search history.

(56) References Cited

U.S. PATENT DOCUMENTS

| | | | | |
|---|---|---|---|---|
| 2007/0098243 A1* | 5/2007 | Gustafson | ............. | G06F 19/321 382/132 |
| 2007/0238948 A1* | 10/2007 | Bartsch | ................ | G06T 7/0012 600/407 |

(Continued)

FOREIGN PATENT DOCUMENTS

| | | |
|---|---|---|
| JP | 2005251091 | 9/2005 |
| JP | 2007058628 | 3/2007 |

*Primary Examiner* — Robert A Sorey (57) ABSTRACT

A non-transitory computer-readable storage medium storing a set of instructions that are executable by a processor, the set of instructions, when executed by the processor, causing the processor to perform operations comprising receiving an imaging study including a medical image of a patient; extracting image context from the imaging study; generating a search query based on the image context; sending the search query to a data source; receiving results of the query from a data source; and providing the results to a user.

17 Claims, 5 Drawing Sheets

(51) Int. Cl.
*G06F 16/9038* (2019.01)
*G06F 16/903* (2019.01)
*G16H 70/20* (2018.01)
*G16H 10/60* (2018.01)

(52) U.S. Cl.
CPC ............ *G16H 10/60* (2018.01); *G16H 30/40* (2018.01); *G16H 70/20* (2018.01)

(56) References Cited

U.S. PATENT DOCUMENTS

| | | | |
|---|---|---|---|
| 2009/0310836 A1* | 12/2009 | Krishnan | G16H 50/70 382/128 |
| 2011/0099032 A1 | 4/2011 | Miyasa et al. | |
| 2012/0020536 A1* | 1/2012 | Moehrle | G06T 7/30 382/128 |
| 2012/0035963 A1* | 2/2012 | Qian | G16H 30/20 705/3 |
| 2012/0130745 A1* | 5/2012 | Jones | G16H 10/60 705/3 |
| 2013/0044925 A1 | 2/2013 | Kozuka et al. | |
| 2013/0311502 A1 | 11/2013 | Takata et al. | |
| 2014/0219500 A1* | 8/2014 | Moehrle | G06T 7/0014 382/103 |
| 2014/0321773 A1 | 10/2014 | Hammon et al. | |
| 2014/0324469 A1* | 10/2014 | Reiner | G16H 50/70 705/3 |
| 2015/0212676 A1* | 7/2015 | Khare | G06F 3/038 715/771 |
| 2016/0232329 A1* | 8/2016 | Xu | G06F 40/186 |
| 2016/0307319 A1* | 10/2016 | Miller | G06T 7/337 |
| 2017/0322684 A1* | 11/2017 | Hermosillo Valadez | G16H 30/40 |

* cited by examiner

Display
300

310 — Pulmonary embolus: MedlinePlus Medical Encyclopedia
www.nlm.nih.gov/.../000132.... ▶ United States National Library of Medicine
311 — A pulmonary embolus is a blockage of an artery in the lung. ... Your health care provider will talk to you about the risk of bleeding problems when you take these ... — 312

320 — Who is at Risk for Pulmonary Embolism? - NHLBI, NIH
www.nhlbi.nih.gov/.../pe/atrisk.... ▶ National Heart, Lung and Blood Institute — 323
321 — Jul 1, 2011 - The risk increases with age. For every 10 years after age 60, the risk of — 322
324 — having PE doubles. Certain inherited conditions, such as factor V ... — 325

330 — Pulmonary embolism - Wikipedia, the free encyclopedia
en.wikipedia.org/wiki/Pulmonary_embolism ▶ Wikipedia — 332
331 — Jump to Risk factors - [edit]. A deep vein thrombosis as seen in the right leg is a risk factor for PE. The most common sources of embolism are proximal leg ...

340 — Thromboembolism Risk Factors - Family Practice Notebook
www.fpnotebook.com/lung/CV/ThrbmblsmRskFctrs.htm ▶
Nov 5, 2014. This page includes the following topics and synonyms: Thromboembolism Risk Factors, Pulmonary Embolism Risk Factors, Deep Vein ...
341        342

METHOD AND SYSTEM FOR CONTEXT-SENSITIVE ASSESSMENT OF CLINICAL FINDINGS

CROSS-REFERENCE TO PRIOR APPLICATIONS

This application is the U.S. National Phase application under 35U.S.C. § 371 of International Application No. PCT/IB2016/050893, filed on Feb. 19, 2016, which claims the benefit of U.S. Provisional Application No.62/120,391, filed on Feb. 25, 2015. This application is hereby incorporated by reference herein.

BACKGROUND

To properly assess the results of medical imaging studies, radiologists and other clinicians must evaluate such studies in the context of a patient's medical history as well as other relevant information. Typically, a radiologist needs to manually query information sources, such as internal data sources or Internet search engines, for background information that may aid in the assessment of the patient's imaging studies. This manual query generation and evaluation of the corresponding results may be a time-consuming process.

SUMMARY OF THE INVENTION

A non-transitory computer-readable storage medium stores a set of instructions that are executable by a processor. The set of instructions, when executed by the processor, causes the processor to perform operations comprising receiving an imaging study including a medical image of a patient; extracting image context from the imaging study; generating a search query based on the image context; sending the search query to a data source; receiving results of the query from a data source; and providing the results to a user.

A system includes a memory storing a set of instructions and a processor executing the ser of instructions to perform operations including receiving an imaging study including a medical image of a patient; extracting image context from the imaging study; generating a search query based on the image context; sending the search query to a data source; receiving results of the query from a data source; and providing the results to a user.

DETAILED DESCRIPTION

The exemplary embodiments may be further understood with reference to the following description and the related appended drawings, wherein like elements are provided with the same reference numerals. Specifically, the exemplary embodiments relate to methods and systems for improving the efficiency of a radiologist's workflow by automatically retrieving information that may be useful in the interpretation of patient medical imaging studies.

Radiographic studies are used in diagnosing a wide variety of medical conditions. A typical radiology workflow involves a radiologist reviewing prior reports to become familiar with the patient's clinical history and analyzing a current imaging study to search for abnormalities. Where abnormalities are found, they may be marked as findings directly on the study images. These findings are typically accompanied by measurements and corresponding descriptions.

Often, a radiologist needs to find additional information to provide proper contextual information with which to assess the patient's images. For example, a radiologist may require information about the distribution of lymph nodes in various sections of the body. Under current practices, the radiologist manually searches information sources (e.g., Internet search engines, electronic encyclopedias, internal documents, etc.) to find relevant information such as signs and symptoms, risk factors associated with a given finding, etc. Information retrieved in this manner must be retrieved in context; for example, a radiologist may observe a lymph node on a computerized tomography ("CT") study of a patient's head, in which case information relevant to the head (e.g., distribution of lymph nodes in the head and neck region, as opposed to, for example, lymph nodes in the hepatic region) must be found. The radiologist then compares retrieved context information to the patient context to determine the relevance of a finding. This is a time-consuming process.

Figure 1:
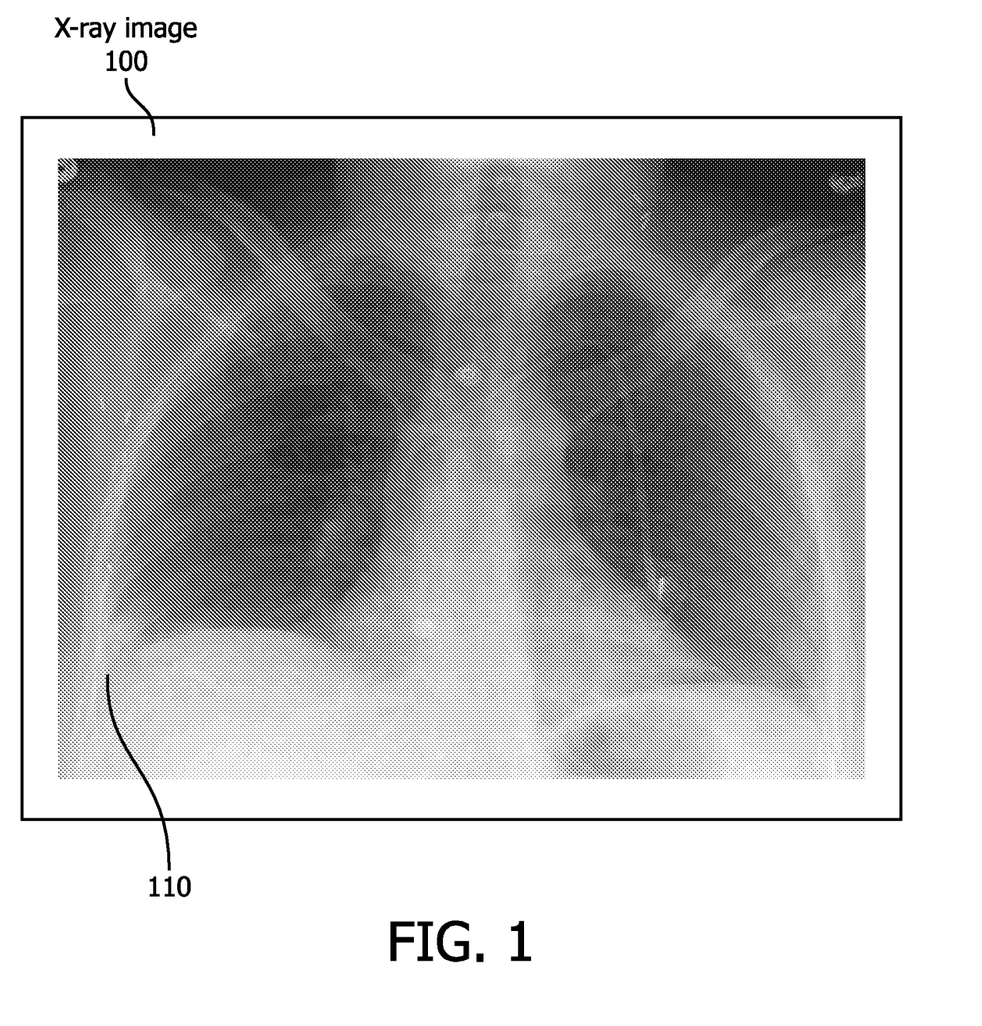
FIG. 1 shows an exemplary medical image that may comprise a portion of a medical imaging study, which may be assessed by the exemplary embodiments.

Considering one example of the above, a radiologist may observe an incidental finding of an emboli on a patient's chest X-ray study. FIG. 1 illustrates an X-ray image 100 showing such an emboli 110. Although a chest X-ray may be insufficient to diagnose the observed abnormality as a pulmonary embolism, it can rule out conditions that mimic this disease based on the patient's context. If the likelihood of a pulmonary embolism is high, the radiologist may recommend that a follow-up CT or magnetic resonance imaging ("MRI") study should be performed on the patient's chest to improve diagnosis. To rule in or out a possible pulmonary embolism, the radiologist may wish to look up risk factors for pulmonary embolisms and signs and symptoms associated with pulmonary embolisms, using knowledge sources such as those described above, and compare this information with the patient's prior reports to evaluate the likelihood of the observed emboli being a pulmonary embolism. As described above, searching for relevant information for the appropriate context (e.g., the patient's prior radiology studies, lab reports, etc.) may be a time-consuming process.

Figure 2:
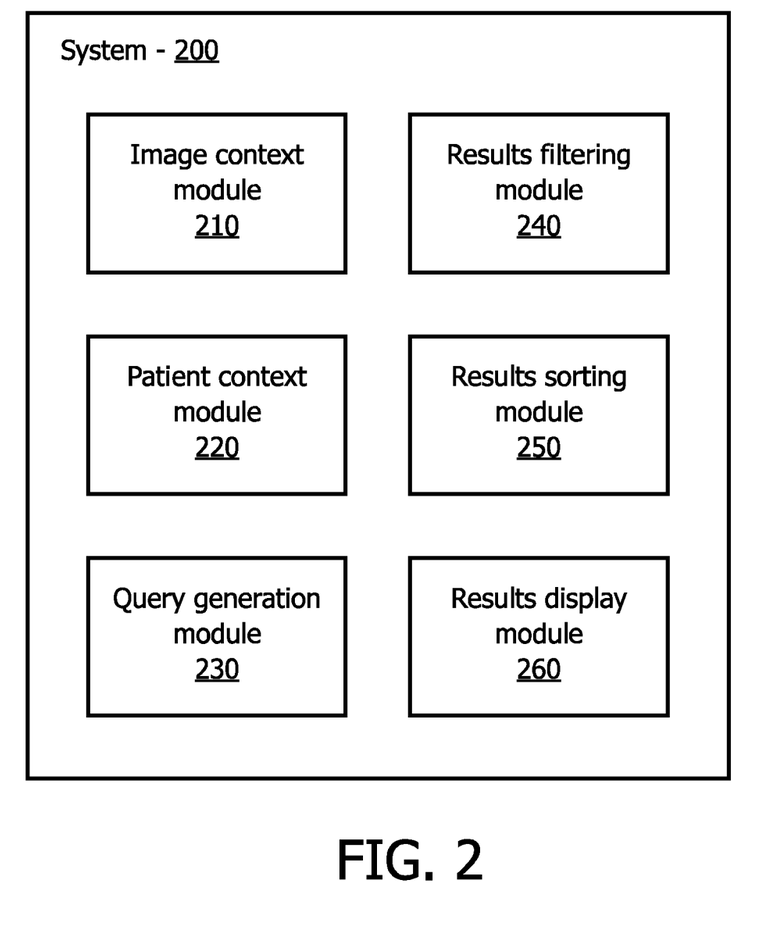
FIG. 2 schematically illustrates a system for performing context-sensitive assessment of medical imaging studies according to an exemplary embodiment.

The exemplary embodiments described herein provide systems and methods whereby the searching for this context information is automated, to speed and simplify the radiologist's workflow. FIG. 2 illustrates, schematically, an exemplary system 200. The exemplary system 200 will be described with reference to a plurality of modules, each of which performs a specific function that will be described hereinafter. It will be apparent to those of skill in the art that a practical implementation of the exemplary system 200 may implement the modules as software, hardware, or a combination thereof, as well as other non-computer-based elements. Additionally, the system 200 will be described in association with the typical functioning of a picture archiving and communication system ("PACS"), an imaging system that provides for viewing and storage of medical images. The PACS may handle and store medical images in accordance with the Digital Imaging and Communications In Medicine ("DICOM") standard.

The system 200 includes an image context module 210. The image context module 210 determines the image context for a current medical image. In one exemplary embodiment, the current medical image is the image currently being displayed to a radiologist or other clinician that is using the system 200. In another embodiment, the current medical image may be an image currently being received from an imaging device (e.g., an X-ray device, CT device, MRI device, etc.) or an image being retrieved from a data storage. The image may be any type of medical image, such as an X-ray image, CT image, MRI image, etc. Thus, although the exemplary embodiments are described with reference to radiological studies, the exemplary embodiments are not limited to radiological images, but may include any type of medical images.

In one embodiment, the current image is displayed in a PACS in conjunction with a corresponding DICOM header. The DICOM header includes information including imaging modality, body part, study/protocol description, series information, orientation (e.g., axial, sagittal, coronal), and window type (e.g., "lungs", "liver", etc.). Additional DICOM fields contain further anatomy-related information concerning the image. These include the DICOM Study Description field corresponding to DICOM tag (0008, 1030), the DICOM Protocol Name field corresponding to DICOM tag (0018, 1030), and the DICOM Series Description field corresponding to DICOM tag (0008, 103e).

In addition to DICOM information about the image, standard image segmentation algorithms may be used to determine the imaging context. These include thresholding, k-means clustering, compression-based methods, region-growing methods and partial differential equation-based methods. In one embodiment, a list of anatomies may be retrieved based on a slice number corresponding to the image and other metadata (e.g., patient age, gender, study description). In such an embodiment, a table may be created that stores, for a large number of patients, corresponding anatomy information for patient parameters (e.g., age, gender) as well as study parameters. This table may then be used to estimate the organ from the slice number and additional information such as patient age, gender, slice thickness, and number of slices. For example, given a slice number 125, female gender, and a "CT abdomen" study description, the table described above may be consulted to identify a list of most likely organs associated with this slice (e.g., liver, kidneys, spleen).

The system 200 also includes a patient context module 220. The patient context module 220 determines characteristics of the patient based on information that may be sourced from multiple data sources, including, but not limited to, reports of prior imaging studies and information from the patient's electronic medical record ("EMR"). Information may be extracted from both study contents and study metadata.

Context information may be extracted from metadata such as DICOM headers of prior studies for the patient. DICOM fields that may be used in this manner include Modality, Body Part Examined, Protocol Name, and Series Description. DICOM information may also include a reason for examination. Because this DICOM field contains a narrative description of the study, a natural language processing ("NLP") engine operative to extract Unified Medical Language System ("UMLS") concepts may be used to extract diagnostic terms from this field. Other DICOM fields from which useful information may be extracted by the patient context module 220 include Procedure Code, Requested Procedure Code, and Scheduled Procedure Code.

Context information and other noun phrases may also be extracted from the contents of prior radiology reports. An NLP engine may be used to determine the sectional structure of prior reports, which may include sections, paragraphs, and sentences. Section headers may be normalized with respect to five classes: technique, comparison, findings, impressions, and none. Excluding section headers, sentences are grouped into paragraphs. The first sentence of each paragraph may be compared against a list of paragraph headers (e.g., LIVER, SPLEEN, LUNGS, etc.). Matching sentences may be marked as being a paragraph header. Additionally, diagnosis-related terms or anatomy-related terms in the Clinical History section of prior reports can be extracted, and dates in comparison studies can be extracted.

In another embodiment, information from relevant prior studies for the patient may be used. Radiologists typically use the most recent relevant report to understand the patient's current status, especially regarding existing findings. Two relevant, distinct prior reports can be used to establish patient context: first, the most recent prior report having the same modality and body part (e.g., a CT study of the patient's head), and, second, the most recent prior report having the same body part (e.g., a further study of the patient's head). Using standard NLP techniques, all noun phrases can be extracted from the Findings sections of the selected reports to aid in establishing patient context.

Additionally, information from the patient's EMR can be extracted when available. This list may include diagnosis, out of which the related body part can also be determined. For example, using an NLP engine to identify Systematized Nomenclature of Medicine ("SNOMED") codes, and a has-finding-site relationship may then be used to identify the related body part.

The system 200 also includes a query generation module 230, which automatically generates search queries. These queries are specific to the context established by the image context module 210 and the patient context module 220. The query generation module 230 may operate a computing device to access a data source (e.g., via the Internet, via a local network, etc.) in accordance with a generated query in a manner that will be described in detail below, so that the radiologist need not manually generate and enter such queries. Queries generated in this manner may easily be viewed by a user of the system 200 if desired, by simply looking at the words comprising the query.

The query generation module 230 may generate queries based on a variety of high-level approaches. In one approach, the query generation module 230 may use the patient context, as determined by the patient context module 220, to augment the imaging context, as determined by the imaging context module 210, and use all this information to generate a query. In another approach, the query generation module 230 may use only the imaging context, as determined by the imaging context module 210, to generate queries, and subsequently use the patient context for filtering. Filtering will be discussed in further detail below.

In one exemplary embodiment, a list of relevant additional documents may be created and stored (e.g., in a database), providing a context-to-knowledge mapping. For example, the additional documents may include a number of documents (e.g., guidelines, lymph node distributions, key images with metadata tags, etc.) related to, and indexed using, referencing indexes such as modality and body part.

In such an embodiment, the imaging context identified by the imaging context module 210 may be, for example, a head CT imaging study, and the query generation module 230 may query this list for appropriate documents indexed with modality=CT and bodypart=head. Appropriate documents may then be provided to the user. In a similar alternative embodiment, a table, rather than a list, may be used.

In another embodiment, a finding description (e.g., "enlarged, necrotic left retropharyngeal LN") may be used directly to query a knowledge source. This knowledge source may be, for example, a general-purpose Internet search engine. Alternatively, the knowledge source may be a specialized, commercial knowledge source, such as STATdx. Results of this query may then be displayed to the user.

In another embodiment, patient context, as determined by the patient context module 220, may also be included as part of a query string to retrieve more specific information. For example, an imaging context including the modality CT and the anatomy "liver" may be combined with a phrase from a relevant prior report (e.g., "reference lymph node") to produce the query string "CT liver reference lymph node," which may be used to query a general-purpose or specialized information source as described above. Identification of relevant phrases from prior reports may be accomplished in a variety of ways. In one exemplary embodiment, patient context module 220 may maintain a list of search phrases that have been manually input by radiologists, and may perform similarity matching on noun phrases extracted from the imaging context. If the similarity is greater than a predefined threshold, the phrase may be deemed relevant. In another embodiment, term frequency-inverse document frequency ("TF-IDF") techniques may be applied to determine the importance of each noun phrases. A predetermined quantity (e.g., five) of noun phrases having the highest TF-IDF score may be deemed relevant.

In another embodiment, user intention may also be included as part a query string. For instance, a user of the system 200 may be interested in seeing images with lymph nodes, in which case the phrase "lymph nodes map" could be added to the query in addition to the imaging and/or patient context information described above. In one embodiment, user intention may be identified based on the user's explicit selection of an option from a menu (e.g., a static or dynamically generated menu) to view search results. In another embodiment, a predefined gesture by the user may be used to indicate what the user is looking for. For example, the predefined gesture may be circling a mouse cursor around a finding of interest, and this gesture may be taken to mean that the user wishes to be shown the lymph nodes around the relevant body part.

The above-described exemplary embodiments may be enhanced by providing patient-specific sorting of the search results. For example, results may be sorted by giving preference to content having the most common information overlap between the retrieved content and the patient context determined by the patient context module 220. Overlap may be determined using various similarity measures such as cosine distance, Euclidean distance, k-nearest neighbor classification, etc.

In another embodiment, a medical ontology (e.g., SNOMED) may be used for filtering and sorting information. The medical ontology may provide a concept-based representation of the patient context and the retrieved information (e.g., as retrieved from a list of internal documents, a general-purpose search, a specialized data source, etc.). Concepts may be extracted from narrative text using concept extraction techniques (e.g., MetaMap). The ontology (e.g., SNOMED) may contain a large set of relationships providing information about how the information contained in the patient context may be related to the information contained in the search results, including commonly used synonyms and acronyms. For example, in some cases, the user's description of a finding may not explicitly describe the location of the finding, and the ontology may be used to match the finding with the correct bodypart by using knowledge about finding location in the body, via the relationship "has-finding-site" along with "is-a" parent-child relationships. Ontological structures may be used along with semantics, which will include synonyms.

Considering one specific example of how this may work, a descriptive label could be: "diffuse, patchy, ground glass opacities with bronchiectasis." Using standard NLP techniques, the concept "bronchiectasis" may be extracted. Using an ontology (e.g., SNOMED Clinical Terms), this concept may then be related to the anatomical site "bronchial structure" via the "has-finding-site" relationship, which itself relates to parent concept "thoracic cavity structure" via the "is-a" relationship.

In another embodiment, the query generation module 230 may generate a search string using a Finding description coupled with preconfigured static text, such as "risk factors" or "signs and symptoms." For example, the concept "pulmonary embolism" may be extracted from the Finding description for a current report. The query generation module 230 may then generate the search strings "risk factors for pulmonary embolism" and "signs and symptoms for pulmonary embolism." These search strings may then be used to search a general-purpose search engine or a specialized knowledge source.

The system 200 also includes a results filtering module 240. The results filtering module 240 receives the results from the performance of the query generated by the query generation module 230. As described above, the results may come from an internal source (e.g., a list or chart providing an index of internal documents that are relevant to the query) or an external source (e.g., a general-purpose Internet search engine or a specialized knowledge source). Once the results have been received, the results filtering module 240 may filter the results to eliminate those that are not relevant. This filtering may be based on the image context, as determined by the image context module 210, and/or the patient context, as determined by the patient context module 220. The context itself may serve as the filter for such filtering; for example, for image context "CT HEAD", filtering will be based on modality=CT and bodypart=HEAD.

The system 200 also includes a results sorting module 250. The results sorting module 250 receives the results of the filtering performed by the results filtering module 240, which may be a relevant subset of the results of the performance of the query generated by the query generation module 230. Results may be sorted based on the image context, as determined by the image context module 210, and/or the patient context, as determined by the patient context module 220. For example, the results may be sorted by giving preference to results having most common information overlap (e.g., based on the number of matching strings of text) with the image context and/or the patient context. In this manner, the sorting may be patient-specific.

The system 200 also includes a results display module 260. The results display module 260 may display the results of the performance of the query generated by query generation module 230, as filtered by the results filtering module 240 and sorted by the results sorting module 250. A variety of different methods for display may be possible. In one exemplary method, results may be displayed with key words or phrases from the patient context highlighted. Words or phrases may be selected by the results display module 260 for highlighting in this manner based on, for example, text matching with the image context and/or the patient context.

Figure 3:
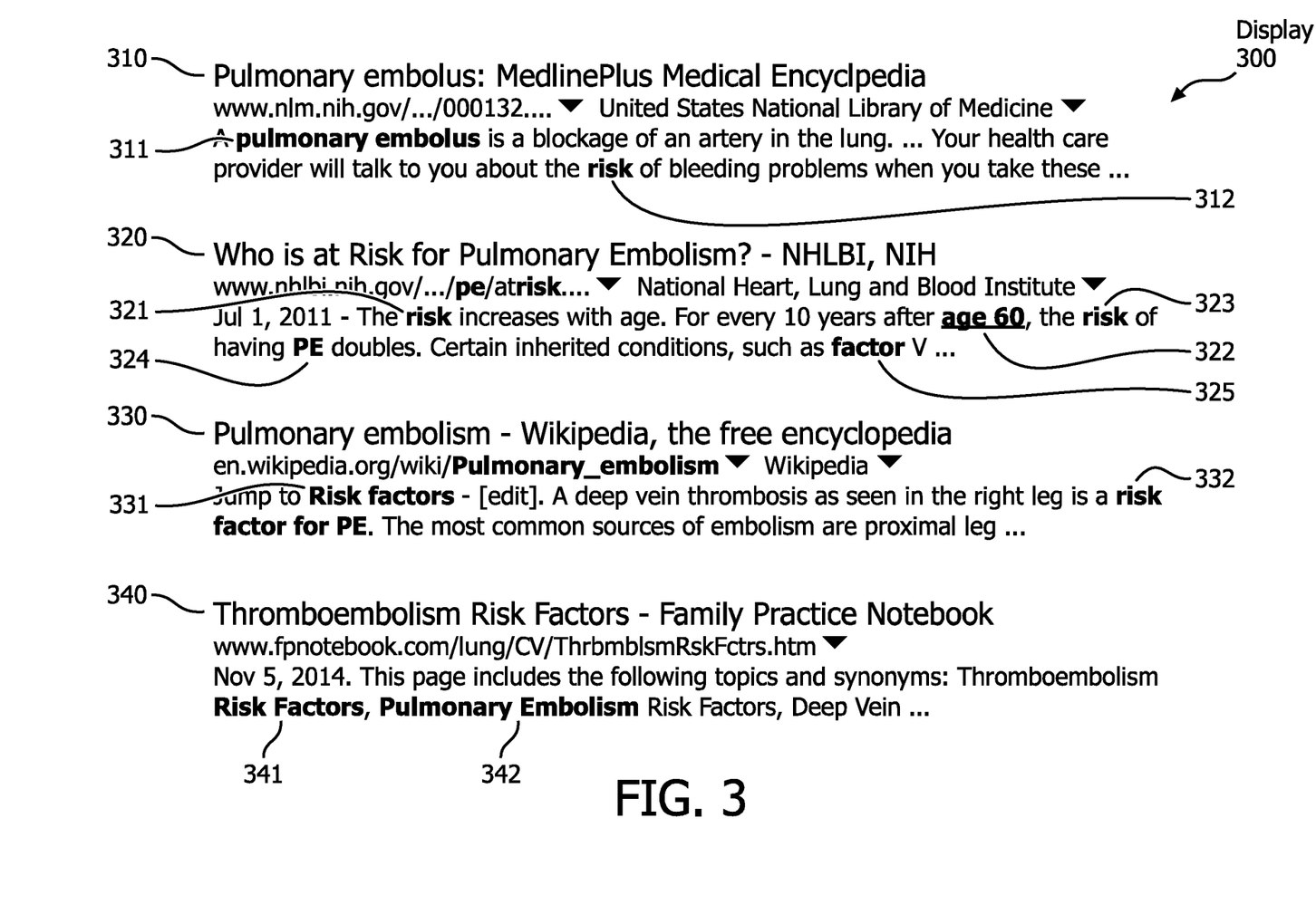
FIG. 3 shows an exemplary display of results that may be provided by the exemplary system of FIG. 2.

FIG. 3 illustrates an exemplary results display 300 that may be generated by the results display module 260. The exemplary results display 300 includes four results 310, 320, 330 and 340, but it will be apparent to those of skill in the art that any number of results may be included in a real-world implementation of a results display. The results included in the exemplary results display 300 may be results that could be produced by a search for "risk factors for pulmonary embolism," and those of skill in the art will understand that the contents of the results display 300 will vary for different search topics. The results display 300 includes four highlights 312, 314, 322, 332, 342 and 352. As described above, the selection of highlights 312, 314, 322, 332, 342 and 352 by the results display module 260 may be made based on matching with key words or phrases from the image context and/or patient context; the highlights 312, 314, 322, 332, 342 and 352 are only exemplary and will vary among differing exemplary embodiments, for different search strings, for matching with different patient inputs, etc.

Figure 4:
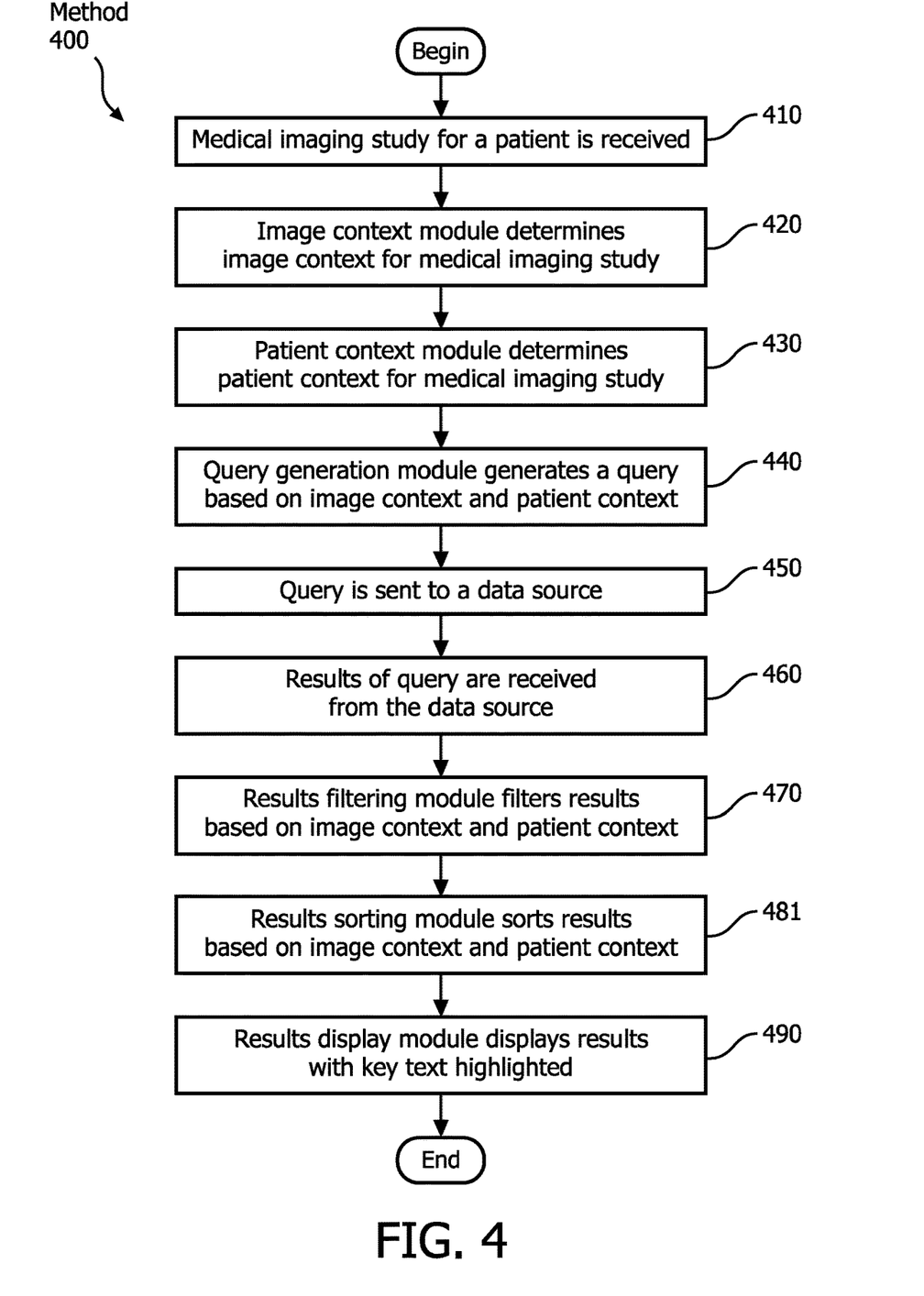
FIG. 4 shows an exemplary method for context-sensitive assessment of medical imaging studies that may be performed by a system such as the exemplary system of FIG. 2.

FIG. 4 shows an exemplary method 400 for retrieving information relevant to a medical imaging study and providing the information to a practitioner. The method 400 will be described with reference to the elements of the exemplary system 200 of FIG. 2, but it will be apparent to those of skill in the art that the method 400 may be performed by any alternative combination of elements capable of doing so. In step 410, a medical imaging study for a patient is received. The modality of the study may be any type of medical imaging study, such as X-ray, CT, MRI, ultrasound, etc. The study may include an image or images, as well as accompanying text in any appropriate format. In one embodiment, the study is formatted according to the DICOM standard.

In step 420, the image context module 210 determines image context for the medical imaging study. As described above with reference to the image context module 210, step 420 may involve textual analysis of the imaging study to extract relevant concepts. In step 430, the patient context module 220 determines patient context for the medical imaging study. As described above with reference to the patient context module 220, step 430 may involve textual analysis of the patient's EMR or other patient medical records to extract relevant concepts.

In step 440, the query generation module 230 generates a query. As described above, the query may typically be generated based on image context determined by the image context module 210. In some exemplary embodiments, the query may also be generated based on the patient context determined by the patient context module 220. In step 450, the query is sent to a data source by the query generation module 230. As described above, the data source may be an internal data source (e.g., an index of internal treatment guidelines, etc.) or an external data source (e.g., a generalized or specific source of data, which may be publicly accessible or proprietary). The submission of the query may be accomplished in any manner that is known in the art. In step 460, results of the query are received by the results filtering module 240. As was the case for the query submission, receipt of the query results may be accomplished in any manner that is known in the art. In some exemplary embodiments, the submission of step 450 and/or the receiving of step 460 may involve the use of an intermediary element, such as a web browser, database access program, etc.; such intermediaries are beyond the scope of the exemplary embodiments and will not be discussed in further detail herein.

In step 470, the results filtering module 240 filters the query results received in step 460. As described above with reference to the results filtering module 240, filtering may be based on the image context determined by the image context module 210 and/or based on the patient context determined by the patient context module 220. In step 480, the results sorting module 250 sorts the results that were filtered by the results filtering module 240 in step 470. As described above with reference to the results sorting module 250, sorting may be based on similarity to the image context determined by the image context module 210 and/or to the patient context determined by the patient context module 220. It will be apparent to those of skill in the art that the filtering and sorting steps are optional, and that, in some exemplary embodiments, one of these steps may be omitted. In one exemplary embodiment, both steps 470 and 480 may be omitted, and the results may be used as they are received in step 460.

In step 490, the results of the query are displayed by the results display module 260. As noted above, the results may be filtered by the results filtering module 240 and/or sorted by the results sorting module 250, or include the same contents and same ordering as in step 460. In some exemplary embodiments, key words or phrases of the results may be highlighted. For example, as described above with reference to the results display module 260, words or phrases matching the image context and/or the patient context may be highlighted. FIG. 3 illustrates a results display 300 that is highlighted in this manner. It will be apparent to those of skill in the art that the bold text used for highlighting in FIG. 3 is only exemplary and that other specific highlighting techniques may be used, including, but not limited to, underlining, italics, different color, differently colored background, different font size, etc. Following step 490, the method 400 ends. The clinician may then use the results that are provided by the method 400 in the same manner that results of manually submitted queries would be used, e.g., to provide proper context for the assessment medical imaging studies. This subsequent use is beyond the scope of the exemplary method 400 and will not be discussed in further detail hereinafter.

In some embodiments, the process of generating search queries and providing results may be influenced by the level of expertise of the radiologist or other user. In such an embodiment, the level of expertise may be determined based on the role of the user that has logged into system 200. The role may be, for example, attending, resident, physician in training, specialist, sub-specialist, or any other role that may be found in a clinical environment. For a user with a lower level of expertise (e.g., a resident or other physician in training), a query may be formulated with search terms appropriate to obtain educational or introductory results (e.g., basic anatomy, disease differential diagnosis, basic disease information, teaching files, etc.). Conversely, a user with a higher level of expertise (e.g., an attending or specialist) may have queries formulated to retrieve up-to-date classification nomenclature/staging information, treatment and/or research options relevant to a particular finding. In another embodiment, a user with a lower level of expertise (e.g., a resident) may have retrieved results sorted to prioritize educational information. In another embodiment, a user with a higher level of expertise (e.g., an attending) may have retrieved results filtered to exclude educational results.

In another exemplary embodiment, the system 200 may be provided with the level of expertise of an ordering health care provider, as opposed to the level of expertise of the immediate user of the system 200. In such an embodiment, the system 200 could provide the user with appropriate management information that could be included in the study interpretation report.

Figure 5:
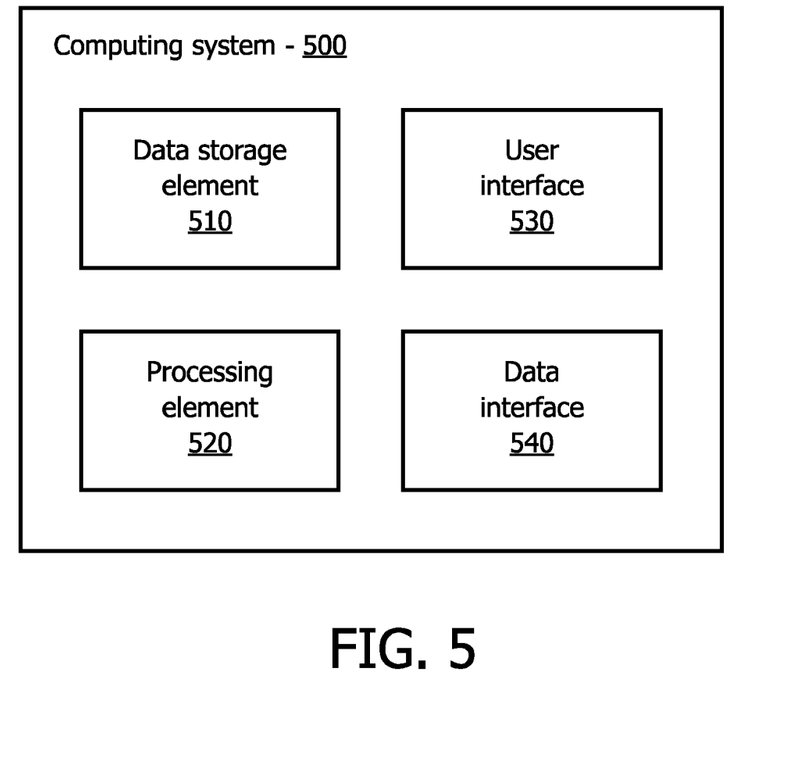
FIG. 5 shows an exemplary computing system that implement the exemplary method of FIG. 4.

FIG. 5 illustrates an exemplary computing system 500 that may implement the exemplary embodiments described above with reference to system 200 and method 400. The computing system 500 includes a data storage element 510 (e.g., one or more hard drives, solid state drives, or other persistent data storage components). The data storage element 510 may store code for implementing the method 400, which may include portions of code performing the functions of the image context module 210, patient context module 220, query generation module 230, results filtering module 240, results sorting module 250, and results display module 260. The computing system 500 also includes a processing element 520, which may include one or more microprocessors capable of executing code such as the code for implementing the method 400. The computing system 500 also includes a user interface 530, which may comprise one or more physical components (e.g., a keyboard, mouse, touchpad, display, touchscreen, etc.) operable to receive user inputs and provide results (e.g., the display 300) to a user. The computing system 500 also includes a data interface 540 (e.g., a wired or wireless connection to a network and/or to the Internet) providing for communications (e.g., the query of step 450 and receipt of query results in step 460) with external data sources. It will be apparent to those of skill in the art that there may be any number of possible implementations of a computing system 500, that such implementations may include additional elements not specifically described above, and that the computing system 500 may be capable of performing additional tasks beyond those described above with reference to the exemplary embodiments.

The exemplary embodiments described above with reference to FIGS. 1-4 may automatically generate search queries based on image context and patient context in a manner approximating the manual generation of queries by a clinician. Such queries may then be performed, and their results evaluated, to provide the clinician with the most relevant information to aid in proper evaluation patients' radiology studies. Because the queries are generated automatically, the radiologist's work flow may be performed in a more time-efficient manner and without any diminution of quality.

Those of skill in the art will understand that the above-described exemplary embodiments may be implemented in any number of matters, including as a software module, as a combination of hardware and software, etc. For example, the exemplary method 400 may be embodied in a program stored in a non-transitory storage medium and containing lines of code that, when compiled, may be executed by a processor.

It will be apparent to those skilled in the art that various modifications may be made to the exemplary embodiments, without departing from the spirit or the scope of the invention. Thus, it is intended that the present invention cover modifications and variations of this invention provided they come within the scope of the appended claims and their equivalents.

What is claimed is:

1. A non-transitory computer-readable storage medium storing a set of instructions that are executable by a processor, the set of instructions, when executed by the processor, causing the processor to perform operations comprising:
   receiving an imaging study from electronic data storage including a medical image of a patient that was received from an imaging device;
   extracting an image context from the imaging study, wherein the image context is extracted from the imaging study using natural language processing to extract a concept from Digital Imaging and Communications in Medicine (DICOM) fields;
   extracting a patient context from at least one of a prior imaging study, information from an electronic medical record, or a list of search phrases manually input by the user;
   automatically generating a search query based on the image context wherein the image context is filtered by the patient context to generate specific patient information, a level of expertise of a user and a user intention, wherein the user intention is based on a predefined gesture by the user, wherein the predefined gesture comprises circling a mouse cursor around a finding of interest in the imaging study, wherein the circling indicates a user intention of being shown other body parts around a body part comprising the finding of interest;
   controlling a computing device to send the search query to a data source via the internet or a local network;
   receiving results of the query from a data source;
   filtering the results based on similarity to the image context or the patient context;
   sorting the results based on information overlap between the retrieved results and the image context or patient context, wherein overlap is determined from at least one of cosine distance, Euclidean distance, or k-nearest neighbor classification; and
   providing the results to the user on a display module.

2. The non-transitory computer-readable storage medium of claim 1, wherein the operations further comprise:
   highlighting relevant text in the results.

3. The non-transitory computer-readable storage medium of claim 1, wherein the medical image includes one of an X-ray image, a CT image, and a magnetic resonance image.

4. The non-transitory computer-readable storage medium of claim 1, wherein the imaging study is formatted according to a Digital Imaging and Communications In Medicine standard.

5. The non-transitory computer-readable storage medium of claim 4, wherein the image context is extracted from a Digital Imaging and Communications In Medicine header.

6. The non-transitory computer-readable storage medium of claim 1, wherein the other body parts comprise lymph nodes.

7. The non-transitory computer-readable storage medium of claim 1 further comprising:
   automatically generating a paragraph header in the imaging study based on the extracted image context and the extracted patient context.

8. The non-transitory computer-readable storage medium of claim 1, wherein the results are highlighted on the display module by using a different colored background.

9. The non-transitory computer-readable storage medium of claim 1, wherein the extracted image context from the imaging study is extracted from a metadata field in the imaging study file.

10. The non-transitory computer-readable storage medium of claim 1, wherein the data source the results are received from is an internet search engine or a commercial knowledge source.

11. The non-transitory computer-readable storage medium of claim 1, further comprising:
   extracting the patient context from a prior imaging study, an information from an electronic medical record, and a list of search phrases manually input by the user; and
   wherein the overlap is determined from a cosine distance, a Euclidean distance, and a k-nearest neighbor classification.

12. The non-transitory computer-readable storage medium of claim 1, the imaging device further comprising:
   an X-ray device, CT device, MRI device, or ultrasound device.

13. The non-transitory computer-readable storage medium of claim 1, wherein the display module is connected to a Picture Archiving and Communication System (PACS).

14. A system, comprising:
   a memory storing a set of instructions; and
   a processor executing the set of instructions to perform operations comprising:
   receiving an imaging study from electronic data storage including a medical image of a patient that was received from an imaging device;
   extracting a patient context from at least one of a prior imaging study, information from an electronic medical record, or a list of search phrases manually input by the user;
   extracting an image context from the imaging study, wherein the image context is extracted from the imaging study using natural language processing to extract a concept from Digital Imaging and Communications in Medicine (DICOM) fields;
   automatically generating a search query based on the image context wherein the image context filtered by the patient context to generate specific patient information, a level of expertise of a user and a user intention, wherein the user intention is based on a predefined gesture by the user, wherein the predefined gesture comprises circling a mouse cursor around a finding of interest in the imaging study, wherein the circling indicates a user intention of being shown other body parts around a body part comprising the finding of interest;
   controlling a computing device to send the search query to a data source via the internet or a local network;
   receiving results of the query from a data source;
   filtering the results based on similarity to the image context or patient context;
   sorting the results based on information overlap between the retrieved results and the image context or patient context, wherein overlap is determined from at least one of cosine distance, Euclidean distance, or k-nearest neighbor classification; and
   providing the results to the user on a display module.

15. The system of claim 14, wherein the operations further comprise:
   highlighting relevant text in the results.

16. The system of claim 14, wherein the medical image includes one of an X-ray image, a CT image, and a magnetic resonance image.

17. The system of claim 14, wherein the imaging study is formatted according to a Digital Imaging and Communications In Medicine standard.

* * * * *